United States Patent
Sunavala-Dossabhoy et al.

(10) Patent No.: US 10,959,852 B2
(45) Date of Patent: Mar. 30, 2021

(54) LOAD DISSIPATING ARTHOPLASTY PROSTHESES

(71) Applicant: Board of Supervisors of Louisiana State University and Agricultural and Mechanical College, Baton Rouge, LA (US)

(72) Inventors: Gulshan Neville Sunavala-Dossabhoy, Shreveport, LA (US); Kevin McCarthy, Shreveport, LA (US)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 132 days.

(21) Appl. No.: 16/162,360

(22) Filed: Oct. 16, 2018

(65) Prior Publication Data
US 2019/0110897 A1    Apr. 18, 2019

Related U.S. Application Data

(60) Provisional application No. 62/572,728, filed on Oct. 16, 2017.

(51) Int. Cl.
| | | |
|---|---|---|
| *A61F 2/36* | (2006.01) | |
| *A61F 2/34* | (2006.01) | |
| *A61F 2/30* | (2006.01) | |

(52) U.S. Cl.
CPC .............. *A61F 2/3662* (2013.01); *A61F 2/34* (2013.01); *A61F 2/367* (2013.01); *A61F 2/3609* (2013.01);
(Continued)

(58) Field of Classification Search
CPC .............. A61F 2002/30563; A61F 2/36; A61F 2/3662–3676; A61F 2002/30014;
(Continued)

(56) References Cited

U.S. PATENT DOCUMENTS 5,181,930 A * 1/1993 Dumbleton ........... A61L 27/443
                                                        623/23.34
5,201,769 A * 4/1993 Schutzer ............... A61F 2/3609
                                                        623/23.22
(Continued)

FOREIGN PATENT DOCUMENTS

FR         2726473 A1 *  5/1996  ......... A61F 2/30907

OTHER PUBLICATIONS

Kate Harrington et al., "The Management of the Symptomatic Patient With a Metal-on-Metal Hip Prosthesis", Canadian Association of Radiologists Journal 67, 2016, p. 76-81.
(Continued)

*Primary Examiner* — Marcia L Watkins
(74) *Attorney, Agent, or Firm* — Davis & Bujold PLLC; Charles G. Holoubek; Michael Bujold

(57) ABSTRACT

A load dissipating arthroplasty prosthesis comprising a shell, an articular device extending into the shell through a collar defined in the sell, a head and neck portion of the articular device extending from the collar, a shaft portion of the articular device extending into the shell, and a plurality of shock absorbing arcuate linkers spacing and allowing limited movement between the shell and the articular device.

19 Claims, 20 Drawing Sheets
(15 of 20 Drawing Sheet(s) Filed in Color)

(52) U.S. Cl.
CPC ....... *A61F 2/30744* (2013.01); *A61F 2/30942* (2013.01); *A61F 2002/30009* (2013.01); *A61F 2002/30014* (2013.01); *A61F 2002/30069* (2013.01); *A61F 2002/30092* (2013.01); *A61F 2002/30324* (2013.01); *A61F 2002/30563* (2013.01); *A61F 2002/30568* (2013.01); *A61F 2002/30571* (2013.01); *A61F 2002/30574* (2013.01); *A61F 2002/30584* (2013.01); *A61F 2002/30589* (2013.01); *A61F 2002/30593* (2013.01); *A61F 2002/30604* (2013.01); *A61F 2002/30621* (2013.01); *A61F 2002/30729* (2013.01); *A61F 2002/3448* (2013.01); *A61F 2002/365* (2013.01); *A61F 2002/3625* (2013.01)

(58) Field of Classification Search
CPC .. A61F 2002/30568; A61F 2002/30069; A61F 2002/30324; A61F 2002/30092; A61F 2002/30584; A61F 2002/30571
See application file for complete search history.

(56) References Cited

U.S. PATENT DOCUMENTS

| | | | |
|---|---|---|---|
| 8,512,413 B2* | 8/2013 | Kellar | A61F 2/32 623/23.41 |
| 9,107,754 B2* | 8/2015 | Kellar | C23C 30/00 |
| 2001/0018616 A1* | 8/2001 | Schwab | A61F 2/30907 623/23.17 |
| 2002/0143402 A1* | 10/2002 | Steinberg | A61F 2/32 623/22.16 |

OTHER PUBLICATIONS

Youngwoo Kim et al., "Treatment of periprosthetic femoral fractures after femoral revision using a long stern", BMC Musculoskeletal Disorders, 2015, 16:113.

* cited by examiner

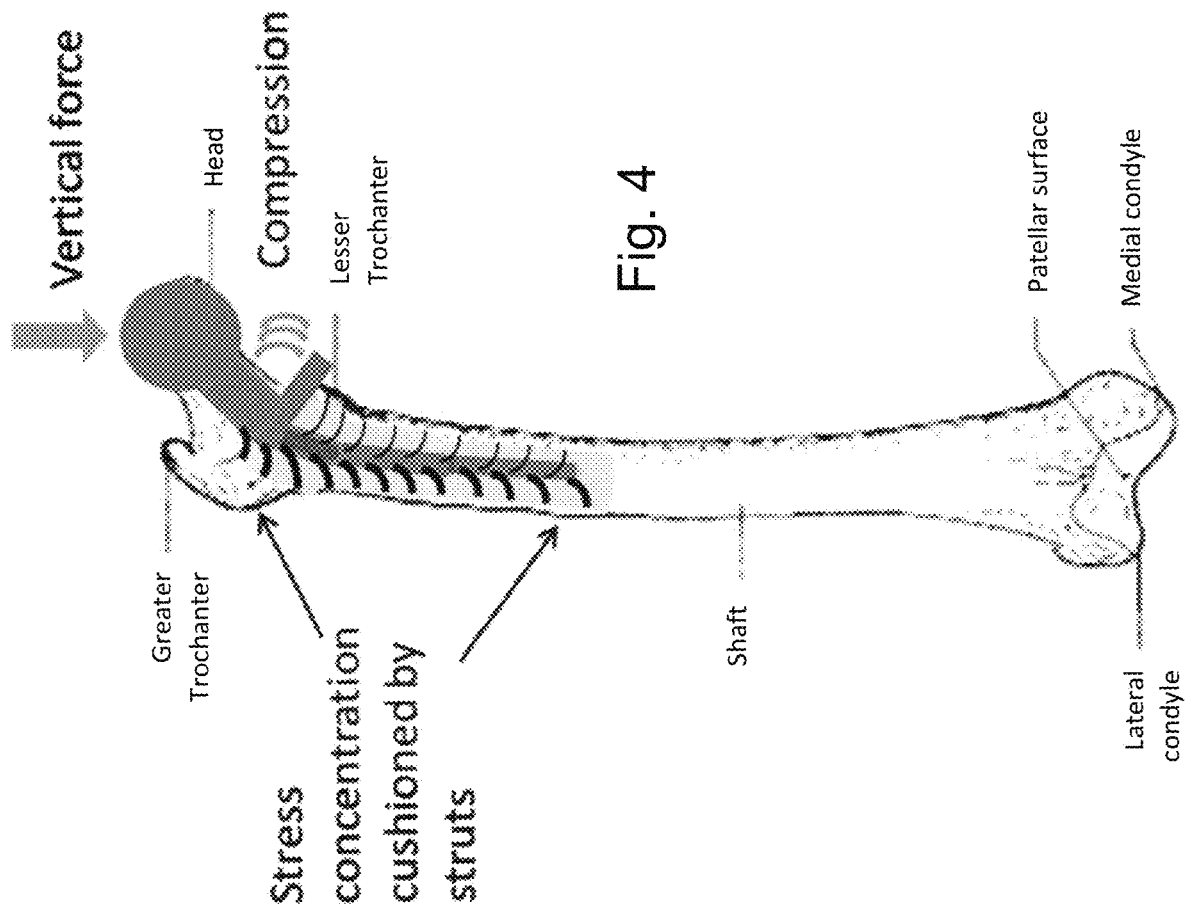

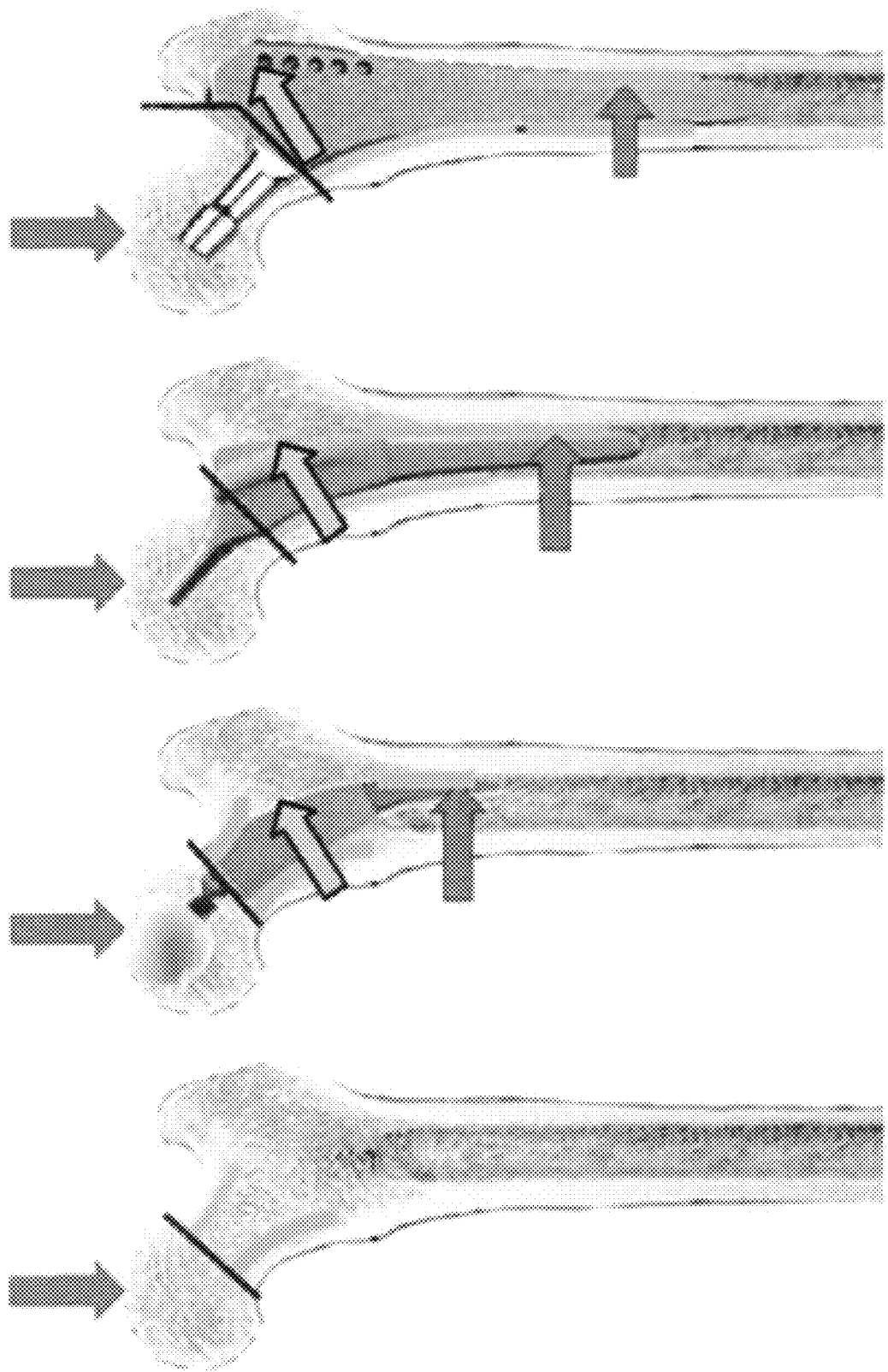

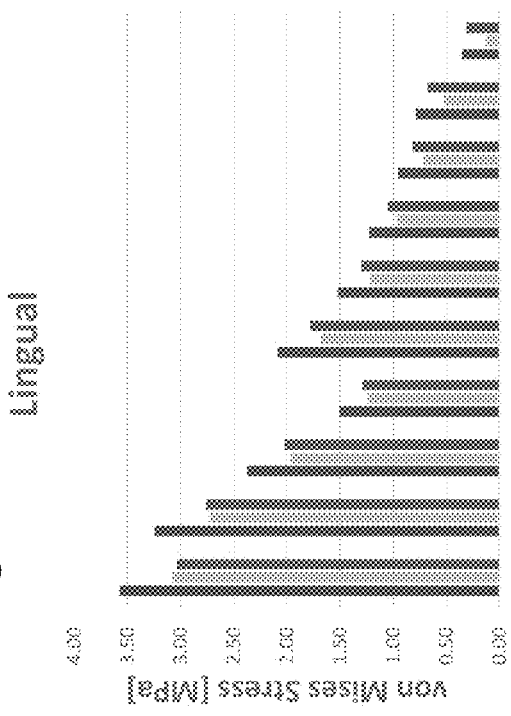
Fig. 10A  PRIOR ART  Buccal
Fig. 10B  PRIOR ART  Lingual
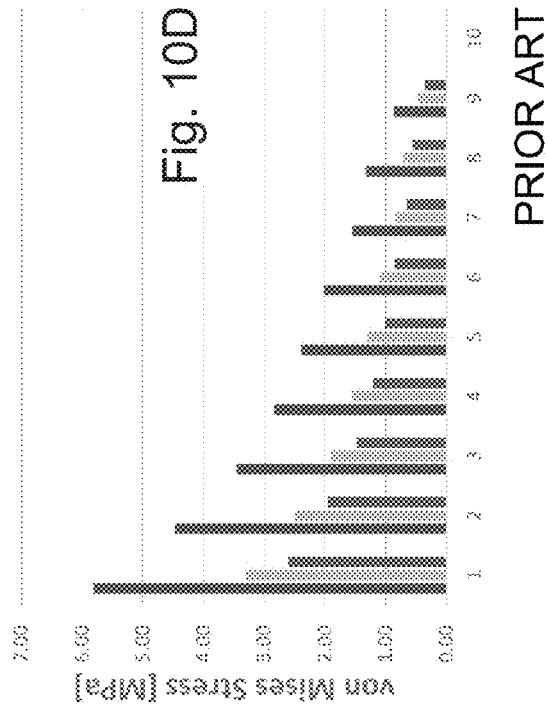
Fig. 10C  PRIOR ART  Mesial
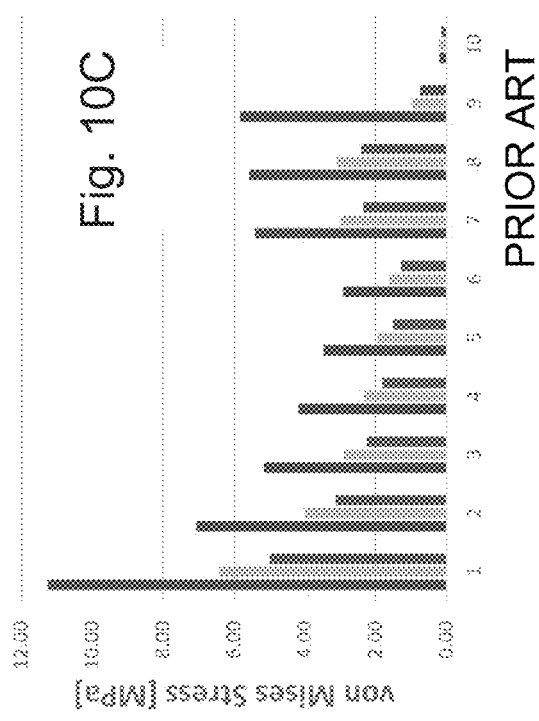
Fig. 10D  PRIOR ART  Distal ■ Rigid
▨ Truss type 1
▧ Truss type 2

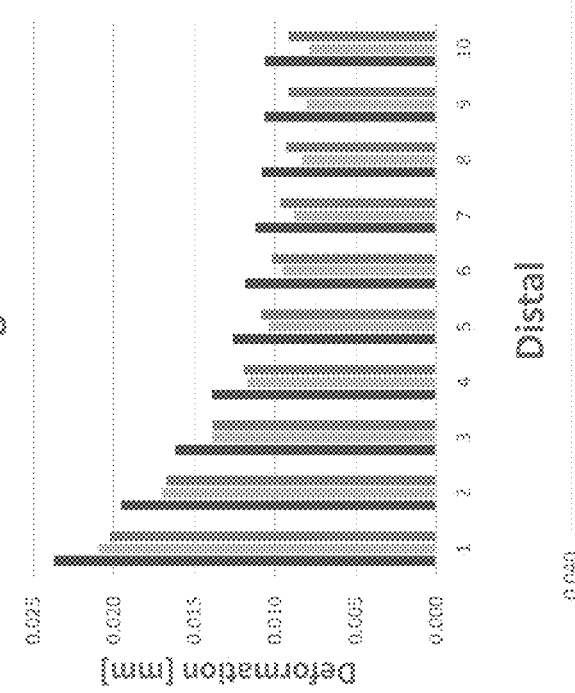
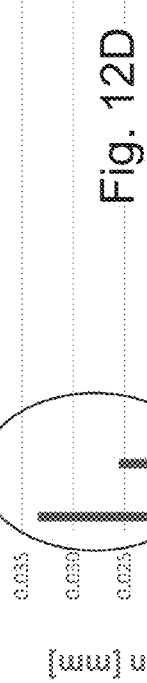
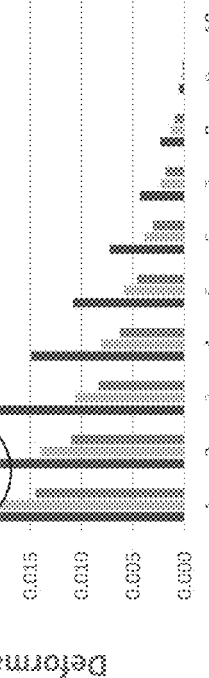
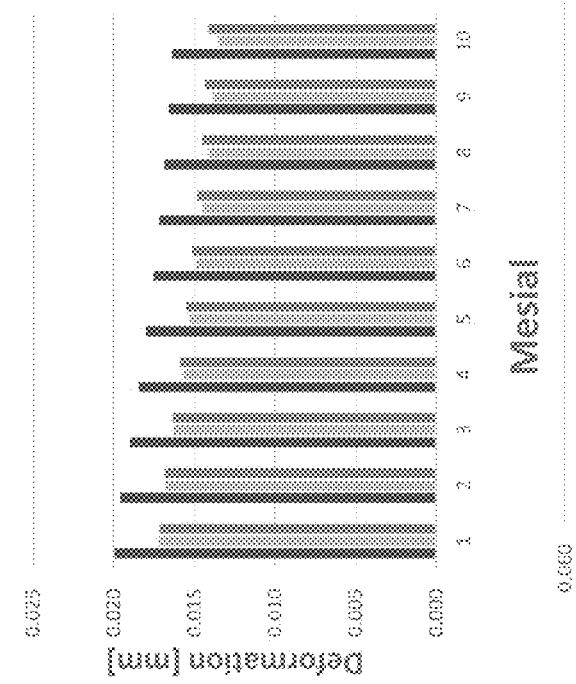
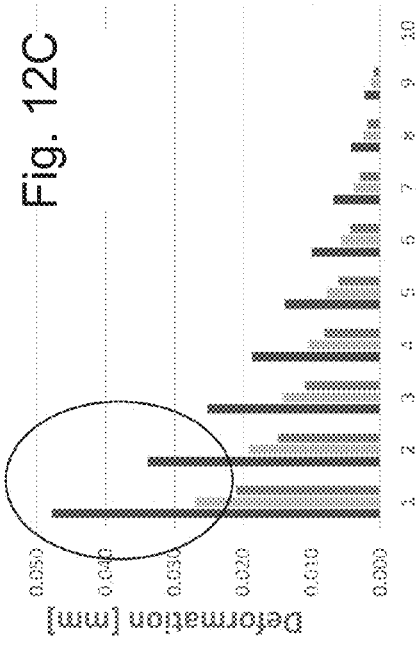

Transverse Section, if truss framework extended at 90°

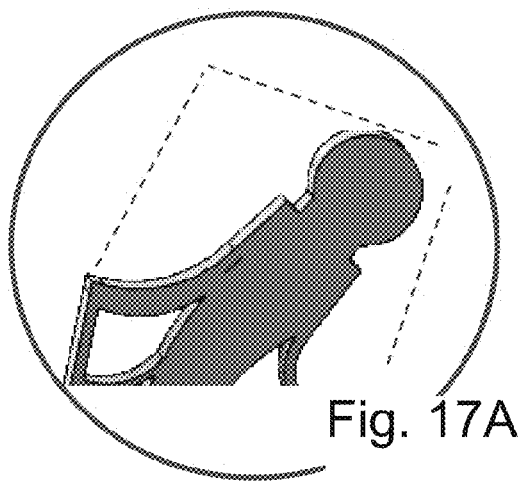

Removable proximal cap can facilitate implant insertion

Fig. 17A

Modifications in truss size, shape, orientation, and number can achieve biologically similar stress/strain distribution at implant/bone interface, and truss framework can be adjusted to support bone health

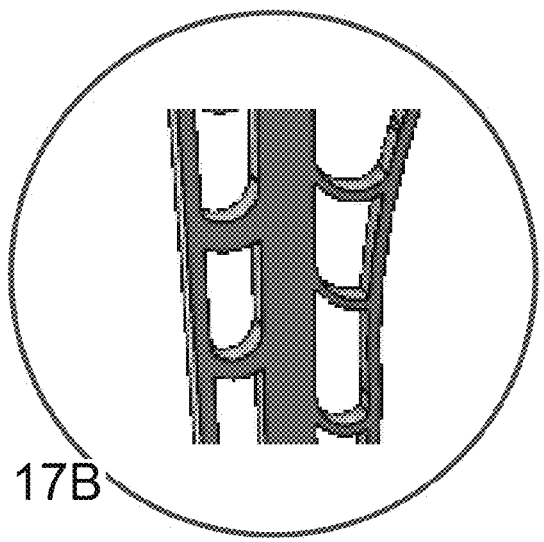

Fig. 17B

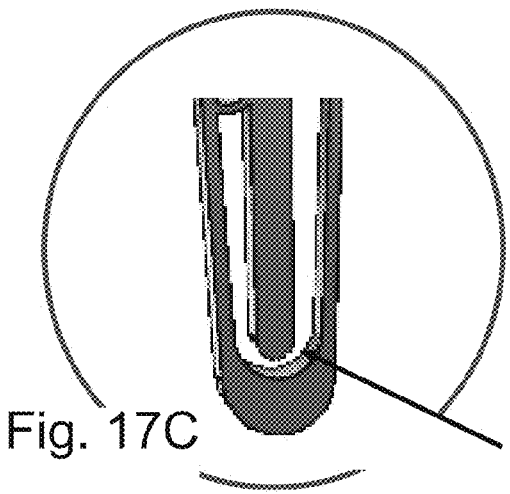

Fig. 17C

Buttressed apical shell can act as a damper

Optimized distance for biosimilar displacement

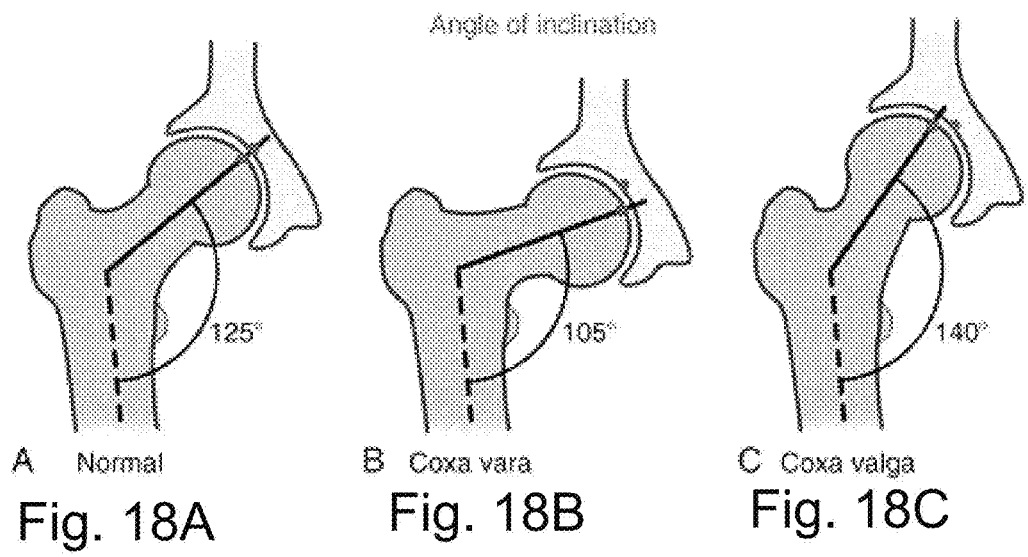
Fig. 18A  A Normal
Fig. 18B  B Coxa vara
Fig. 18C  C Coxa valga
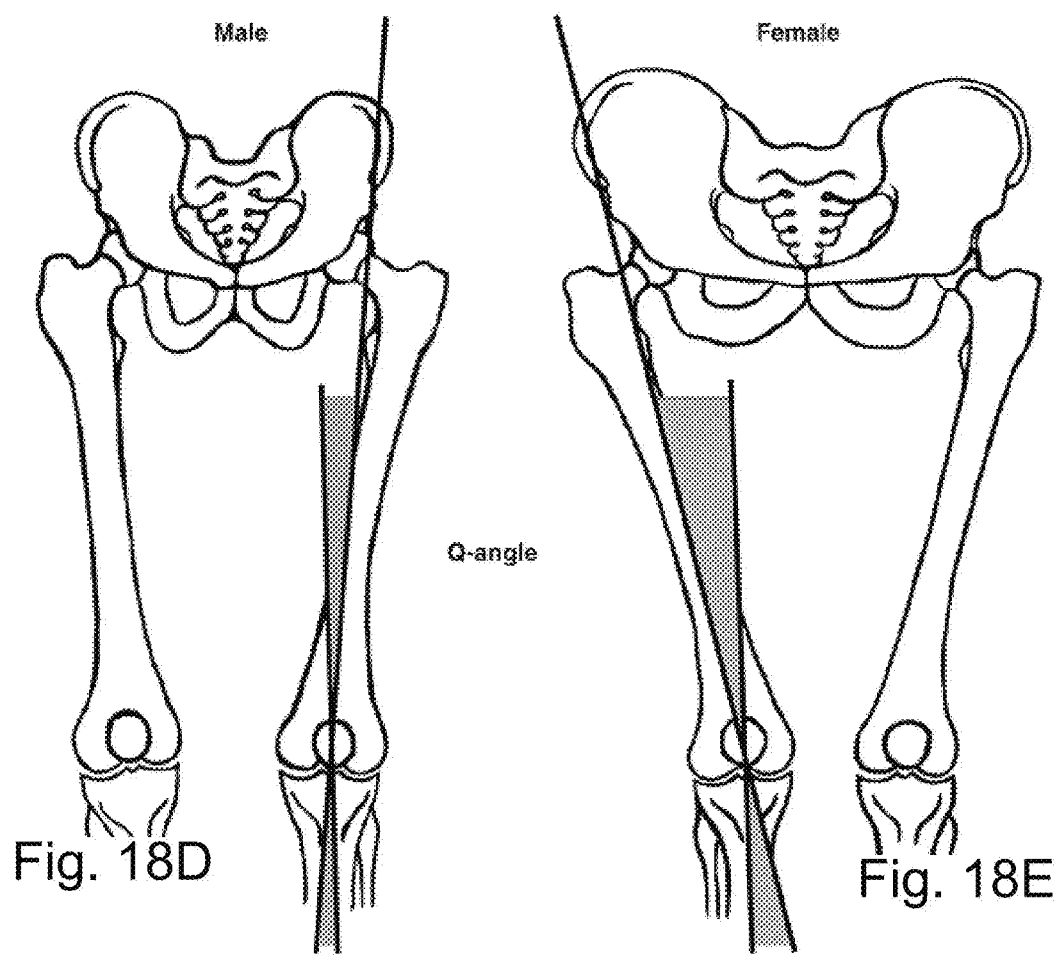
Fig. 18D
Fig. 18E

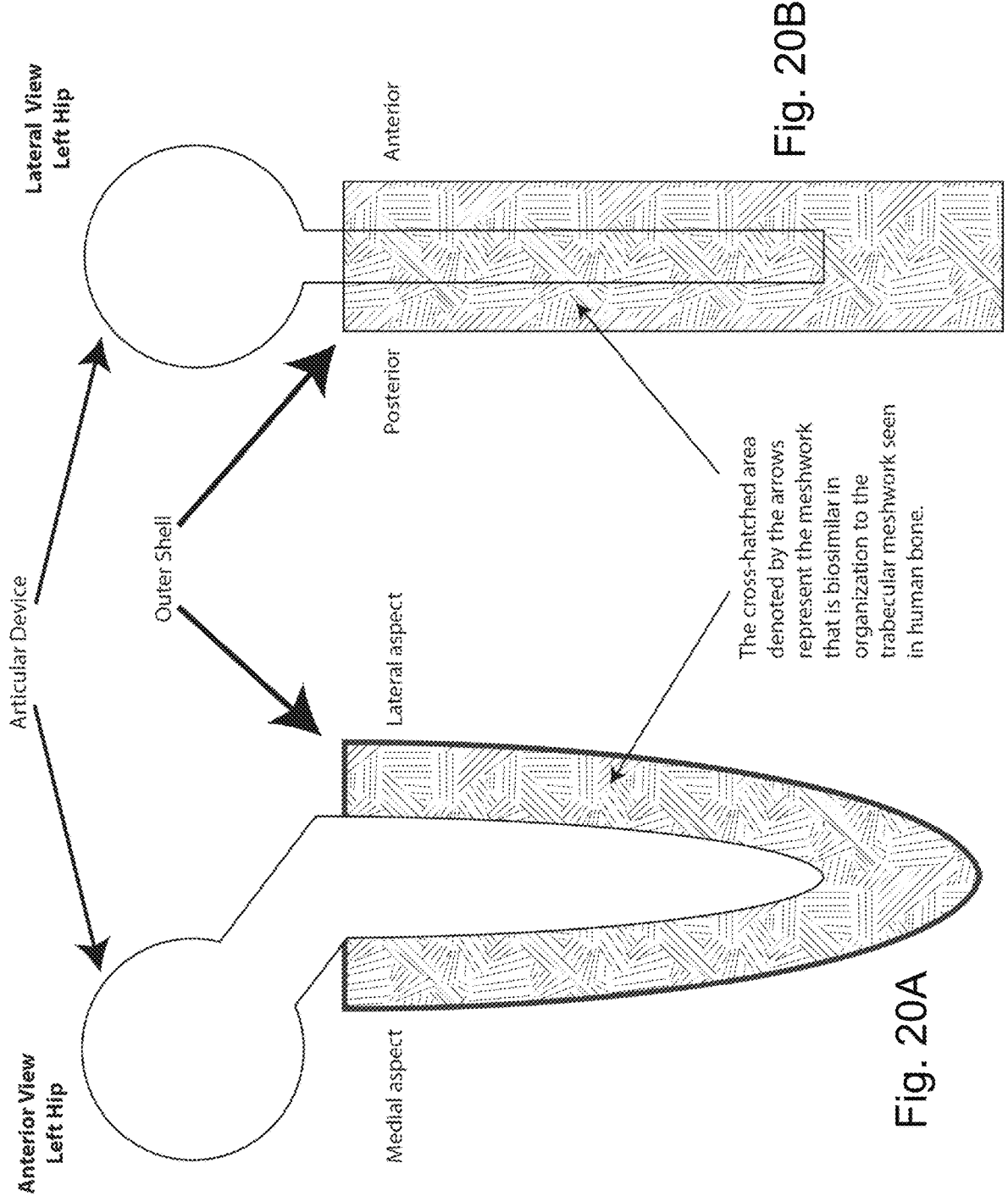

LOAD DISSIPATING ARTHOPLASTY PROSTHESES

CROSS REFERENCE TO RELATED APPLICATIONS/PRIORITY

The present invention claims priority to United States Provisional Patent Application No. 62/572,728 filed Oct. 16, 2017, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Despite an aging population, with a growing and pressing need for hip replacement prosthesis, current technology for hip replacement all too often leads to failure.

SUMMARY

Wherefore, it is an object of the present invention to overcome the above mentioned shortcomings and drawbacks associated with the current technology.

The bones and joints of the human body are subject to impact forces at heel strike during normal gait. The skeletal load is transmitted from the pelvis (hip) to the lower extremities through the femoral head. In healthy individuals, the articular cartilages that cover the femoral head and line acetabulum and the synovial fluid within the joint cushions the compressive load before its transfer to the shaft. Hip arthroplasty (total or hemi-arthroplasty) is a surgical treatment offered to patients suffering from irreparable joint damage caused by diseases such as arthritis, avascular necrosis, and benign tumors, and in cases of femoral neck fractures. Total arthroplasty involves the replacement of the femur head (ball) and the acetabulum (socket), whereas hemi-arthroplasty is the reconstruction of the femur head alone. Arthroplasty prostheses are typically constructed of metal, ceramic or plastic, and total arthroplasty components can be metal (ball)-on-metal (socket), metal-on-ceramic, metal-on-plastic, ceramic-on-ceramic, or ceramic-on-metal. Although conventional hard metal/ceramic-on-metal/ceramic implants sustain less wear and tear, the direct transmission of forces from the metal on bone causes chronic inflammation, fibrosis, pseudo tumors, and vasculitis (Harrington 2016, Koper 2016). Concerns regarding fracture of ceramic liner, metal debris, and periprosthesis bone fractures (Kim 2015, Maloney 2015) lead to the design of a newer generation prosthesis that have a polyethylene acetabulum liner or an elastomeric liner between the femur head and the acetabulum cap. But, rapid wear and osteolysis are major limitations to their use (Das 2016). Most modern implants emulate the anatomy of the femur with the head connected to a tapered femoral stem with, or without, a platform and lateral fins. However, failure of the hip prosthesis to effectively dissipate or absorb impact forces leave the bone susceptible to undesirable force concentration and therefore, implant mobility and, or, bone fracture. Peri-prosthetic femoral fractures of the shaft and greater trochanter region are increasingly common, and they are a significant complication to revision surgery.

To improve patient comfort, extend the longevity of the prosthesis and avert undesirable peri-implant fractures and adverse reactions, the invention redesigns the hip arthroplasty prosthesis to effectively redistribute impact stresses making the implant more biomechanically compatible and durable. The strategic placement of arcuate linkers to absorb and redistribute impact forces, thereby reducing the risk of peri-implant mobility and, or, fracture.

The present invention also relates to a load dissipating arthroplasty prosthesis comprising a shell, an articular device extending into the shell, and a shock absorber spacing and allowing limited movement between the shell and the articular device. According to further embodiments, the shock absorber includes a plurality of arcuate linkers. According to further embodiments, a collar covers an upper portion in the shell. According to further embodiments, a first end of at least one of the plurality of arcuate linkers is attached to a shaft portion of the articular device and a second end of the at least one of the plurality of arcuate linkers is attached to one of an inner surface of the shell and an inner surface of the collar. According to further embodiments, the plurality of arcuate linkers attach to the shaft at a plurality of circumferential locations along the shaft and a plurality of axial locations along the shaft. According to further embodiments, the articular device passes through a collar aperture, the collar aperture being defined in the collar. According to further embodiments, the collar aperture is located in a substantially radially central location on the collar. According to further embodiments, the shell has notches arranged along a circumference of the shell to engage with pins of a cap, the cap providing a point of impact to secure the prosthesis into a femur of a mammal. According to further embodiments, the arcuate linkers attach to the shell and to the shaft with pedicel portions, the pedicel portion being one of wider, thicker, and both wider and thicker than a middle portion of the arcuate linkers. According to further embodiments, the collar forms an upper membrane on the shell. According to further embodiments, a lowest portion of the shaft is proximate to but spaced from a closest inner surface of the shell, such that under normal load, the lowest portion of the shaft does not impact the inner surface of the shell. According to further embodiments, the central shaft resiliently moves between 0.1 mm and 3.0 mm with respect to the shell when a force of between 700 to 5000 Newtons is applied to the shaft. According to further embodiments, the collar is made of one of titanium metal and a titanium alloy. According to further embodiments, a plurality of medial arcuate linkers attach a medial facing portion of the shaft to a medial portion of the shell, and a plurality of lateral arcuate linkers attach a lateral facing portion of the shaft to a lateral portion of the shell. According to further embodiments, the plurality of lateral arcuate linkers are one of greater in number, greater in size, and constructed out of a less flexible material than the plurality of medial arcuate linkers, or some combination thereof. According to further embodiments, the shell has an outer surface that includes one of a porous metal and trabecular constructions. According to further embodiments, the porous metal is one of titanium, tantalum, and an alloy including one titanium, tantalum, and both titanium and tantalum. According to further embodiments, the porous metal is one of a foam and coated with one of calcium phosphate, hydroxyapatite, derivatives of calcium phosphate, derivatives of hydroxyapatite, and combinations including one or more thereof. According to further embodiments, a Z axis is defined by the shaft, wherein the shaft is rotationally fixed about the Z axis with respect to the shell, allowing the central shaft to resiliently increase obliquity about the collar aperture.

The invention further relates to a load dissipating arthroplasty prosthesis comprising a shell, an articular device extending into the shell through a collar defined in the sell, a head and neck portion of the articular device extending from the collar, a shaft portion of the articular device extending into the shell, a plurality of shock absorbing arcuate linkers spacing and allowing limited movement between the shell and the articular device, a first end of the plurality of arcuate linkers attaches to the shaft at less than 45 degrees, as measured from an attachment location on the shaft, and a second end of the plurality of arcuate linkers attaches to the shell at less than 45 degrees, as measured from an attachment location on the shell.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various embodiments of the invention and together with the general description of the invention given above and the detailed description of the drawings given below, serve to explain the principles of the invention. It is to be appreciated that though some of the accompanying drawings are drawn to scale, the emphasis is instead placed on illustrating the principles of the invention. The invention will now be described, by way of example, with reference to the accompanying drawings in which:

FIG. 4 is a side view of the load dissipating arthroplasty prosthesis of FIG. 3, inserted in a femur bone, showing forces experienced during use;

FIGS. 8A to 8D are cross sectional views of peri-implant stress concentration within the femur with varying conventional implant designs and femoral stem lengths. Weight bearing forces on the condylar head (shown as vertical red arrows) create stress concentration at the distal aspect of the femur shaft (red horizontal arrows) and the greater trochanter (yellow arrows) regions;

FIGS. 10A-10D are bar graphs of modelled solid-form or truss-based dental implants in a mandibular bone segment. In a 2D Finite Element Analysis, von Mises stresses were calculated in crestal bone that was segmented into 10 regions—1 being bone abutting the implant to 10 being the bone furthest away from the implant. As observed, higher von Mises stress was observed in bone adjacent to rigid implants than truss-based implants especially, at mesial and distal aspects;

FIGS. 12A-12D are bar graphs based on the model of FIGS. 10A-10D, showing increased stress and bone deformation go hand in hand. And, as observed, crestal bone deformation is significant around mesial and distal aspects of rigid, solid-form implants (circles);

FIG. 17A is an up close view of an upper portion of the load dissipating arthroplasty prosthesis of FIG. 14, with dashed red lines indicating a proximal cap of FIG. 2, FIG. 17B is an up close view of a midsection of the load dissipating arthroplasty prosthesis of FIG. 14, and FIG. 17C is an up close view of a lowest portion of the load dissipating arthroplasty prosthesis of FIG. 14;

FIGS. 18A-18C are cross sections of three different angles of inclination, and FIGS. 18D-18E are cross sections of different Q-angles;

FIGS. 20A and 20B are anterior cross section and lateral partial cross section views of a further embodiment of a load dissipating arthroplasty prosthesis.

DETAILED DESCRIPTION

Figure 1:
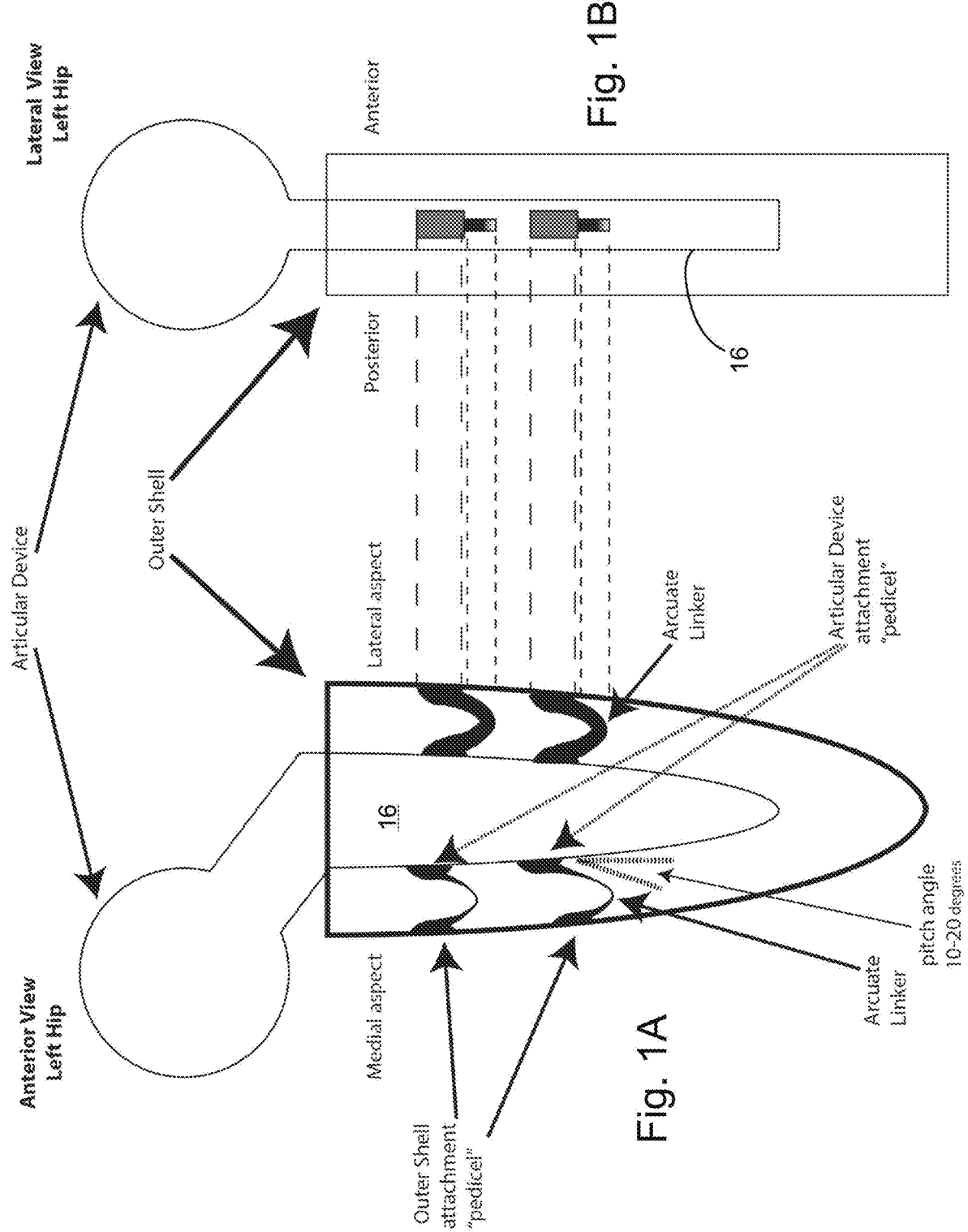
FIG. 1A is an anterior cross section view of a load dissipating arthroplasty prosthesis according to the presently claimed invention.
FIG. 1B is a lateral partial cross section view of the load dissipating arthroplasty prosthesis of FIG. 1A.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1A-20B, a brief description concerning the various components of the present invention will now be briefly discussed. As can be seen in this embodiment, the load dissipating arthroplasty prosthesis 2 preferably comprises an articular device 4, a shell 6, and a shock absorber 8. The articular device 4 preferably comprises a head 10, a neck 12, a mesial fin 14, and a shaft 16. The shell 6 preferably includes a collar 18 and a cap 20. The collar could be formed of the same material as the rest of the unit but relatively thin, functioning more as an encapsulation than a functional support. Alternative, the collar could be a post manufacturer encapsulation of an FDA approved polymeric material, such as a subtype of propylene.

Shell: The shell will preferably provide a fluid tight envelope between the interior of the shell and the exterior environment exterior to the shell. The shell can be seen as an outer portion of the load dissipating arthroplasty prosthesis. The outer surface of the shell is preferably a metal, such as titanium or tantalum, or non-metal, such as ceramic. The metal would preferably have or be covered with a trabecular or porous structure. The metal may be substantially pure or as an alloy. The metal may be as a foam and/or coated with calcium phosphate, hydroxyapatite, derivatives of each or combinations including one or more thereof and or other materials to encourage the formation of vascular systems within the porous area and integration into the bone. The inner surface of the shell defines a void into which the shaft extends. A terminal end of the shaft is spaced from the inner surface of the shell in both the vertical and horizontal directions. The interior of the shell could be a vacuum, or filled with air, foam, an inert gas, an inert liquid, or a gel, for example. The inner surface of the shell could be lined with an antimicrobial substance to prevent microbial growth.

Collar: The collar provides an upper membrane to the interior of the shell. The collar is preferably resiliently flexible and water tight—such a titanium sheet metal. The shaft passes through a collar aperture in the approximate center of the collar. The collar aperture being a through aperture passing through the collar. The collar is preferably rotationally fixedly secured and sealed to the shell along the circumference of the collar. According to a preferred embodiment, the collar along with the shaft, the arcuate linkers, and the shell will be cast as a fluid tight single unit. According to a further embodiment, a silicon seal may seal the shaft to the collar aperture.

Shock Absorber: The shaft is resiliently but flexibly supported via one or more shock absorbers to allow limited movement with respect to the shell. In the embodiment shown, the shaft is supported by a plurality of arcuate linkers. The arcuate linkers, similar in some embodiments to leaf springs, are attached on a first end to the shaft and on a second end to one of the inner surface of the shell, or an inner surface of the collar, or both, preferably via pedicels, described below. The arcuate linkers are preferably attached in numerous locations around the circumference of the shaft and along the axial length of the shaft to provide uniform force dissipation. The arcuate linkers may be of all the same resiliency, thickness, flexibility, and resistance, or there may be some variation among any or some combination of those qualities among multiple arcuate linkers, to provide for some controlled initial movement with a lower amount of force, and additional controlled movement with increased force, or to allow for more movement in a first direction than in a second direction, or to provide for uniform movement in multiple directions with a uniform number of arcuate linkers. In the embodiment shown in FIG. 1A, the arcuate linkers stop approximately mid-way down the length of the shaft, it is envisioned that the arcuate linkers may continue substantially completely down the length of the shaft. The arcuate linkers will preferably be of sufficient strength that they will prevent the shaft from touching the inner surface of the shell under normal to extreme loads forces. The arcuate linkers are preferably metal formed of titanium and/or titanium alloy, and/or a resiliently flexible non-metal materials, including polymers and carbon nano-fibers. The arcuate linkers may be of unitary construction with the shaft and/or the shell.

The arcuate linkers allow for the shaft to move in three dimensions to take pressure off of the bone, in the X, Y, and Z directions, where, +, −Z directions are the axial direction defined by the shaft, and the +, −X and +, −Y directions are two axis that are perpendicular to one another and that are also perpendicular to the Z axis. The three dimensional shock absorption spreads the impact force over an increased length of time and more evenly dissipates the force over a larger area of the shell and thus the bone, decreasing microfractures, fibrous tissue formation, and bone resorption and failure of the load dissipating arthroplasty prosthesis.

The arcuate linkers and the remainder of the load dissipating arthroplasty prosthesis could be 3D printed, which would convey many benefits, including easy personalization of the load dissipating arthroplasty prosthesis for the patient.

It is anticipated that the maximum flexing or movement of the shaft with respect to the shell will be preferably less than 5.0 mm, more preferably under 1.0 mm under normal loads—between 700 and 6000 Newtons per hip joint.

While preferably the multiple arcuate linkers shown help prevent metal fatigue over the life of the load dissipating arthroplasty prosthesis 2, alternative embodiments include a micro-chip enabled strain gauge on or adjacent to the network of arcuate linkers. The micro-chip would preferably be connectable via wireless technology to alert or give a status as to the health or potential failure of the arcuate linkers and even the load dissipating arthroplasty prosthesis itself if separation from the bone begins to occur.

It is anticipated that the collar may act as a shock absorber as well, flexing inwards toward the interior of the shell and outward away from the interior of the shell in response to force placed on the load dissipating arthroplasty prosthesis.

It is anticipated that the shaft may pivot, in a rotationally fixed manner, around the femoral stem axis in the collar, allowing for more controlled movement and more even dissipation of force from the head to the shaft through the shock absorber to the shell and then the bone.

Alternative embodiments of the shock absorber that may be used instead of or in addition to the arcuate linkers or one another include a hydraulic shock absorber. The hydraulic shock absorber embodiment would preferably be between the lower central portion of the inner surface of the shell and the lowest portion of the shaft to provide one dimension of controlled movement. Additional hydraulic shock absorbers may be used in between the side of the inner surface of the shell and the side of the shaft to give additional dimensions of movement.

A further additional embodiment of the shock absorber would use coiled springs. The coiled springs would be preferably attached to the circumference of the shaft and the inner surface of the shell. Preferably the springs would be attached at least three or more circumferential locations around the shaft. Preferably, an additional one or more coiled springs would be placed between the lower central portion of the interior of the shell and the lowest portion of the shaft to provide resilient shock absorption in the most direct line of mandibular force—along the Z direction. The lowest portion being the portion furthest away from the head.

The shock absorber is preferably an arcuate linker with an attachment pedicel (foot). The broad attachment foot at the medial and lateral aspect of the unit provide additional surface area for the attachment of the arcuate linker segment. The shape/size of this pedicel can be varied with the shape/size of the arcuate linker.

The arcuate linker is the actual force displacement mechanism of the device, the curvature of the arc absorbing the displacement forces that are passed through the articular device to the shell (also called the outer shell). The degree of arch, the thickness, and the width of the arcuate arch can be varied according to anticipated loading. The number and distribution of these units can be varied.

A pitch angle preferably has a range between 4-30 degrees, more preferably between 10-20 degrees from vertical, and is most preferably at or around 18 degrees. The pitch angle is that angle between the articular device and one-half of the arcuate linker.

The inventors discovered that too steep of a pitch angle, for example, 45 degrees or greater, can lead to premature fracture of the attachment points of the arcuate linker to the pedicels. The shallower pitch angle, approaching 0 degrees, places each arm of the arcuate linker closer to relative vertical, but also requires more space in the interior of the shell, which is limited. To resist fracture, each arm is preferably as close to vertical as possible, allowing for the transduction of forces to be directed downward into the actual arch structure without any major deformation occurring at the site where the arcuate linker arms meet the pedicels. By doing so, the arch is forced to act as a potential shock absorber.

The arrangement of the pedicels can vary. The medial pedicel does not have to be directly across from the lateral pedicel. They can be offset. The offset would serve to change the shape of arch. The arch, the portion of the arcuate linker between the two pedicels, itself can be varied in thickness. In the figure, a thicker arch is shown n the lateral aspect of the drawing compared to the medial aspect. The thicker arch would still flex but would have a significantly enhanced resistance to flexing. In this model the inventor predicted that the thicker arches would be necessary to dampen the lateral loading of the hip while walking (due to the angle of the ball interacting with the socket). The arches on the medial aspect could be made thinner since loading would be predicted to be more moderate. Moreover, the thickness of the arches along the length of the arch can be variable in itself. Instead of thicker lateral arches, the lateral arches could be the same thickness but increased in number, could be wider, and/or could be made of a less flexible material than the medial arches.

The number of arcuate linkers can be variable in number, and the organization and arrangements of the arcuate linkers can be variable. The model shown here is a simplification of the concept of the device. In practice, it is anticipated that the manufacturer would be given either a CT scan or MRI scan of the patient's hip. From there the manufacturer can extract the actual 3D structural data and then build the hip in silico. From there manufacturer can then superimpose a "blank" prosthetic implant into the articular region to test fit the implant into the in silico patient hip. Once the hip angulations are set, manufacturer can then modify the organization and structure of the struts based on patient parameters (e.g. age, weight, activity ect) to come up with a device that would fit the patient's morphometric and physiometric parameters. Much of the structure and organization of the arcuate linkers could be imputed from Finite Element Analysis Algorithms driven by a focused Artificial Intelligence subroutine.

A study by Rudman et al. assessed the distribution of stress in proximal human femur. A 2D finite element model of the femur was developed in which acetabulum and ligamental forces were included. Regions of higher trabecular bone density in the proximal femur were assigned a higher modulus than the surrounding trabecular bone. The 2D model shows that when increasing loads are applied to the distal femoral shaft, there is the generation of compressive stresses (blue) on the mesial aspect of the condylar head and neck, whereas tensile strain (red) at the lateral aspect including the greater trochanter region.

Peri-implant fractures are common in conventional hip implants. Compressive forces distributed along the condylar head and mesial aspect of conventional solid form hip implants create increased strain at the lateral aspect of the femoral shaft. This invariably leads to bone fracture near the greater trochanter region or femoral shaft (image on right and x-rays that show the fractures).

However, the most common failure is aseptic loosening of the hip implant. Resorption of bone abutting the implant leads to implant mobility. It constitutes 75% of cases that undergo hip revision surgery.

Hip implant failure is due at least partially to the differing modulus of elasticity of metal implant and bone. However, there are 2 schools of thought whether the failure is a result of—1) Excessive Stress build-up at bone interface that leads to bone resorption, implant loosening and eventually, bone fracture, (Unyielding solid-form implants cause increased stress at bone interface leading to bone resorption, implant loosening, and implant/bone fracture), or 2) Stress Shielding where the implant bears much of the load leading to surrounding bone atrophy and fracture (Most of the load is borne by the implant, and not surrounding bone, leading to bone atrophy and bone fracture. The inventors favor the viewpoint of bone resorption being due to excessive stress build-up, and the inventors' data on dental implants support this thought.

We modelled solid-form or truss-based dental implants in a mandibular bone segment. In a 2D Finite Element Analysis, von Mises stresses were calculated in crestal bone that was segmented into 10 regions—1 being bone abutting the implant to 10 being the bone furthest away from the implant. As observed, higher von Mises stress was observed in bone adjacent to rigid implants than truss-based implants especially, at mesial and distal aspects.

Increased stress and bone deformation go hand in hand. And, as observed, crestal bone deformation is significant around mesial and distal aspects of rigid, solid-form implants. This is exactly what is observed clinically; bone loss around conventional dental implants begins with loss of interdental bone.

We have applied a similar truss-suspension mechanism to the new hip implant concept. Our novel hip implant design can overcome the limitations associated with conventional implants namely, loss of bone integration, fractures, and osteonecrosis of the acetabulum. Moreover, our concept can be readily incorporated into existing 3-D printed femoral stems.

Outer aspects of the new hip implant will look similar to those that are already on the market. It will preferably have a condylar head, a femoral neck and stem, and a mesial fin. Cross sections of the implant show an outer shell and arcuate linkers/truss framework that suspends the shaft (to which the neck and condylar head is attached) to the shell.

An advantage of one embodiment is that it can be easily customized, and the truss framework can be adjusted to support bone health. Modifications in arcuate linker size, shape, orientation, and number can achieve biologically similar stress/strain distribution at implant-bone interface. Additionally, the distance between the shaft and shell (including an apical portion of the shell) can be optimized to attain a biosimilar displacement. In addition, the apical aspect of the shell can be buttressed to act as a damper.

Figure 2:
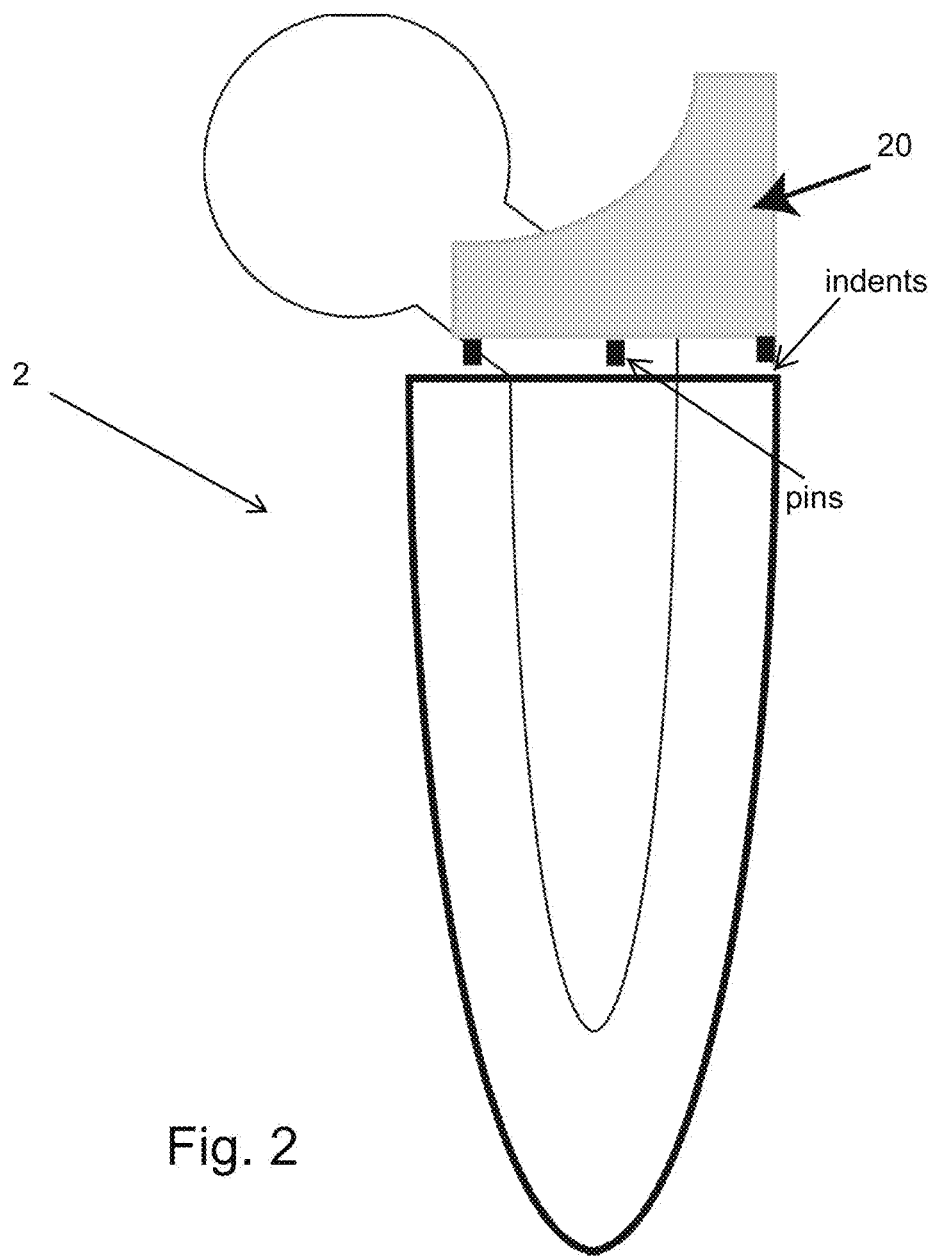
FIG. 2 is an anterior cross section view of a load dissipating arthroplasty prosthesis of FIG. 1A, with a side view of a cap about to engage with the shell of the anterior cross section view of a load dissipating arthroplasty prosthesis.
Figure 3:
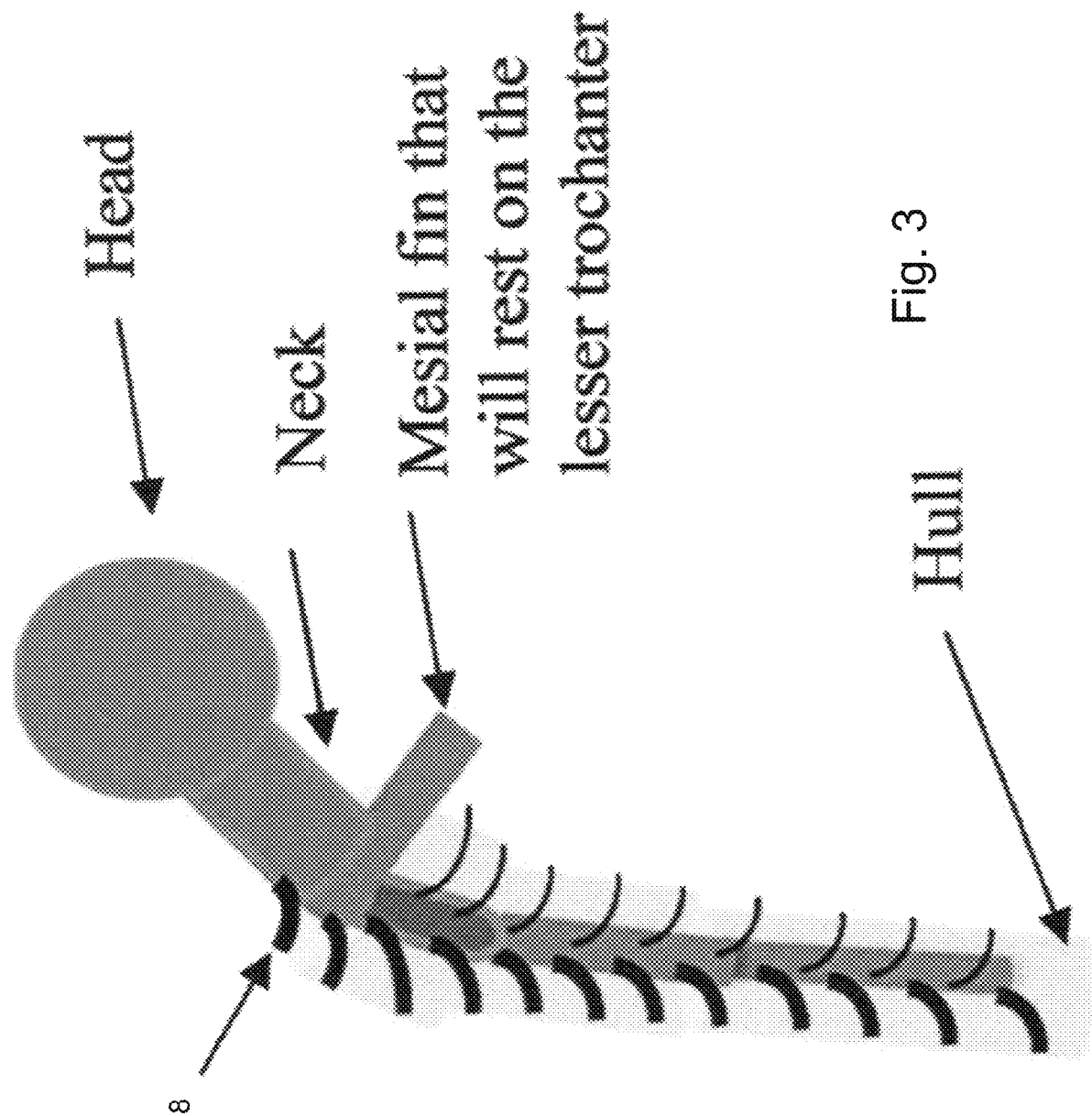
FIG. 3 is an isometric partial see through view of a second embodiment of a load dissipating arthroplasty prosthesis.
Figure 5B:
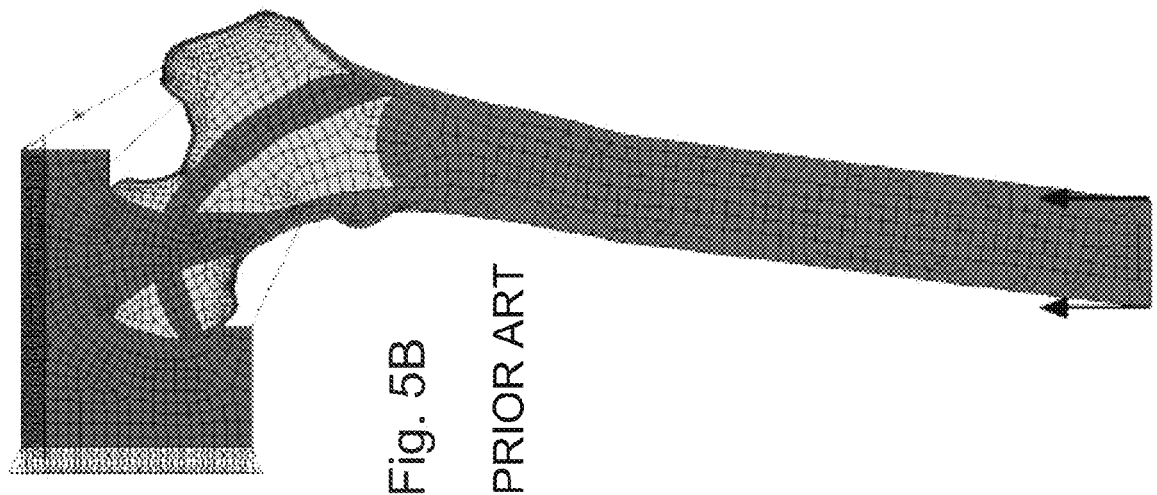
FIG. 5B is a 2D finite element model of the femur in which acetabulum and ligamental forces were included.
Figure 5A:
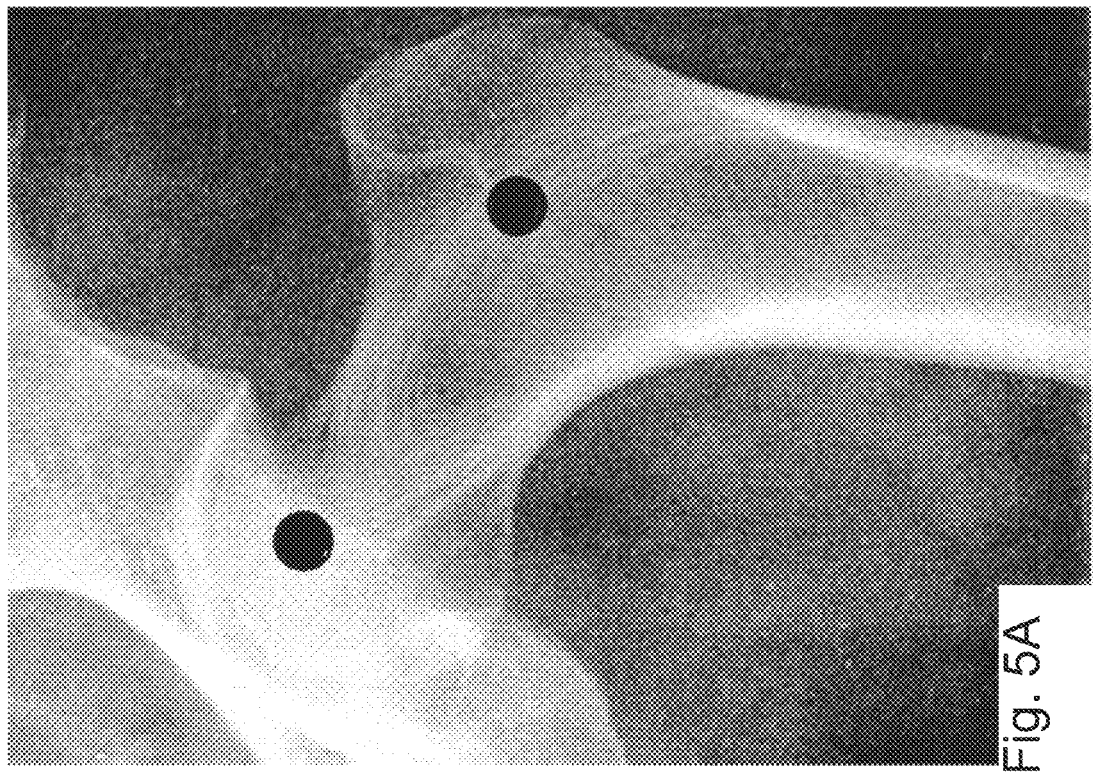
FIG. 5A is an x-ray of human femur.
Figure 6:
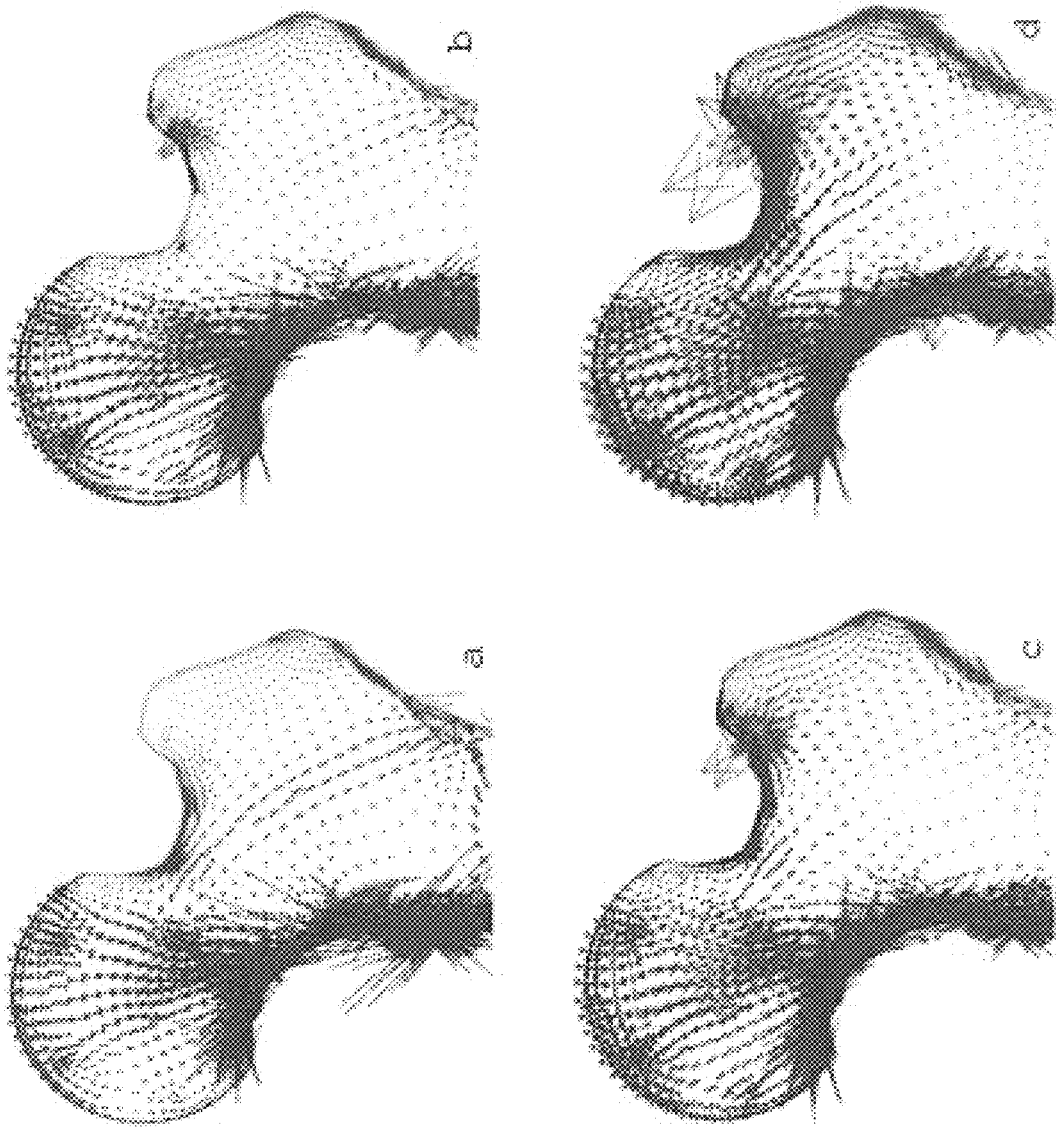
FIGS. 6A to 6D are models of stress distribution upon femur head loading, with increasing degree of compressive forces to the head of the femur from FIG. 6A to FIG. 6D result in dispersion along the lesser trochanter and mesial aspect of the femur shaft (shown in blue), whereas opposing tensile forces (shown in red) are at the greater trochanter and distal aspect of the shaft.
Figure 7C:
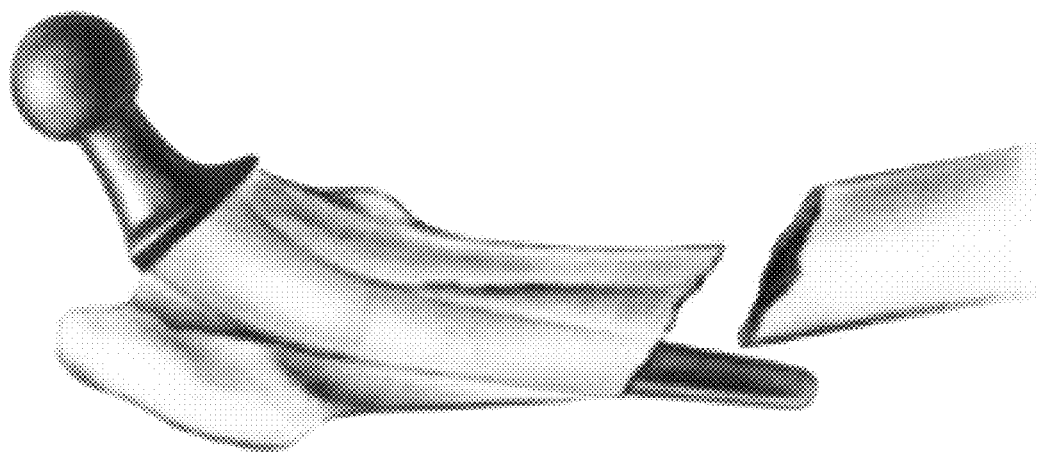
FIGS. 7A to 7C are different examples of common peri-implant fractures with conventional implants.
Figure 7B:
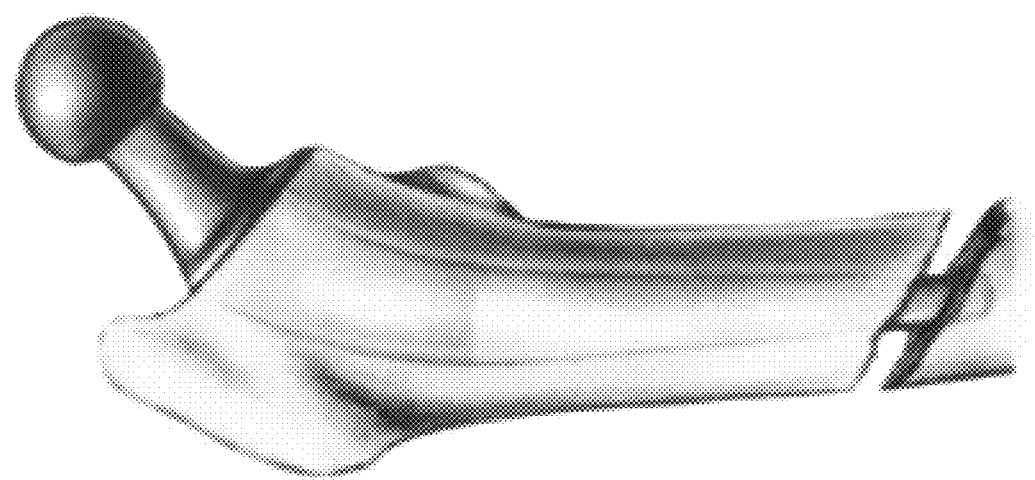
Figure 7A:
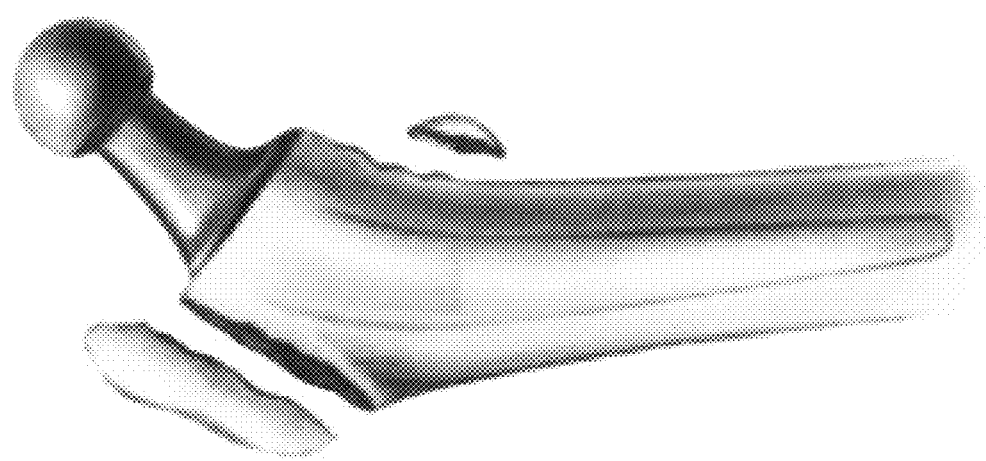
Figure 9B:
FIGS. 9A and 9B are x-rays of bone fracture near the greater trochanter region or femoral shaft with conventional implants.
Figure 9A:
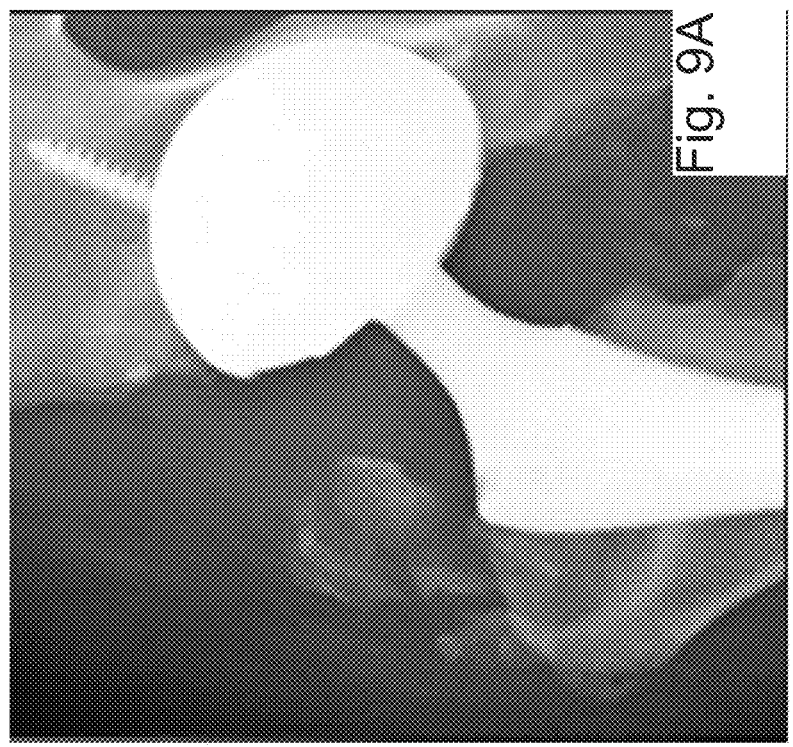
Figure 11B:
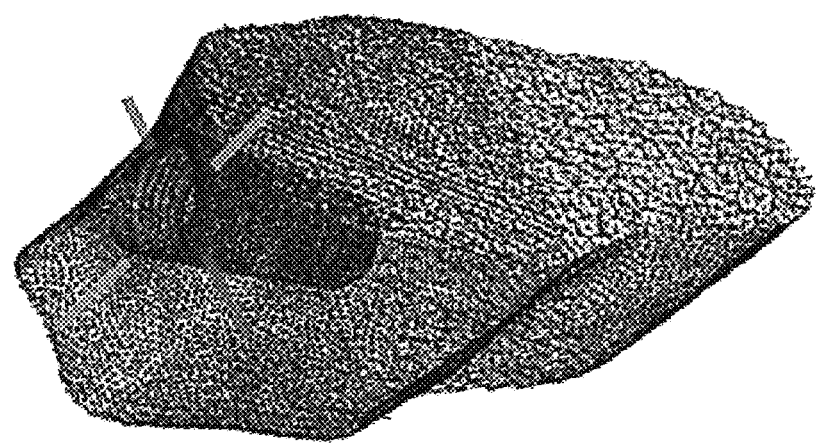
FIG. 11A is an x-ray of a conventional dental implant where observed bone loss around the implants begins with loss of interdental bone and FIG. 11B is a representation of the computer modelled solid-form or truss-based dental implants in a mandibular bone segment.
Figure 11A:
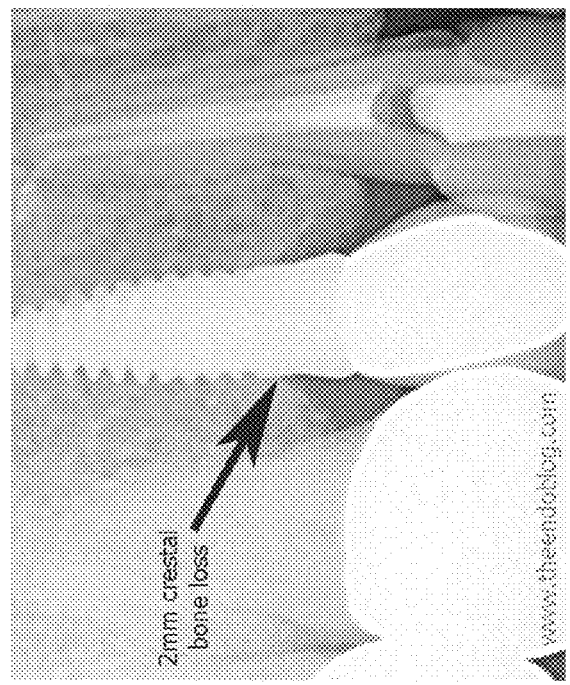
Figure 13:
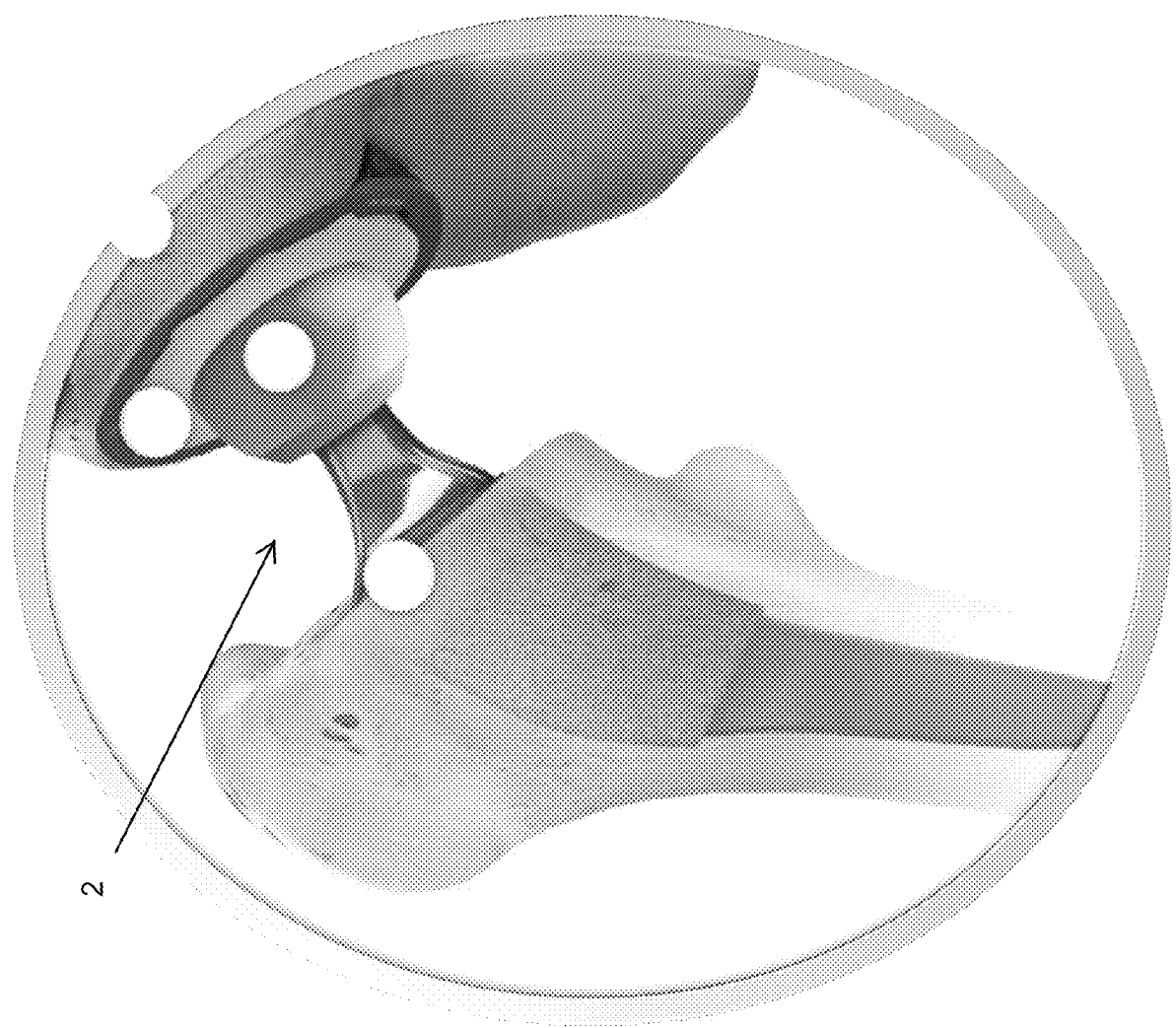
FIG. 13 is a partially cut out isometric view of the load dissipating arthroplasty prosthesis of FIG. 1A.
Figure 14:
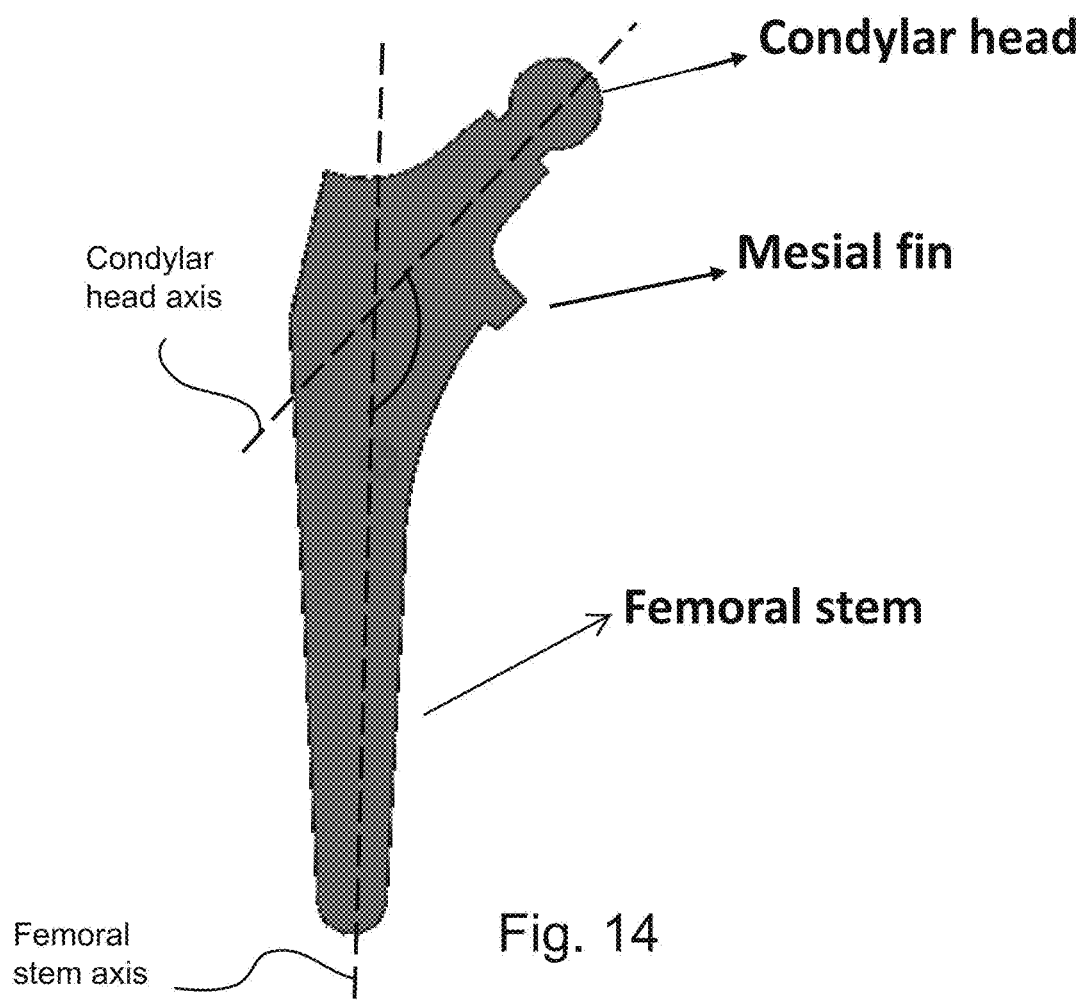
FIG. 14 is a flat plan view of the further embodiment of the load dissipating arthroplasty prosthesis, with a condylar head axis and a Femoral stem axis, and the angle their intersection forms, shown.
Figure 15:
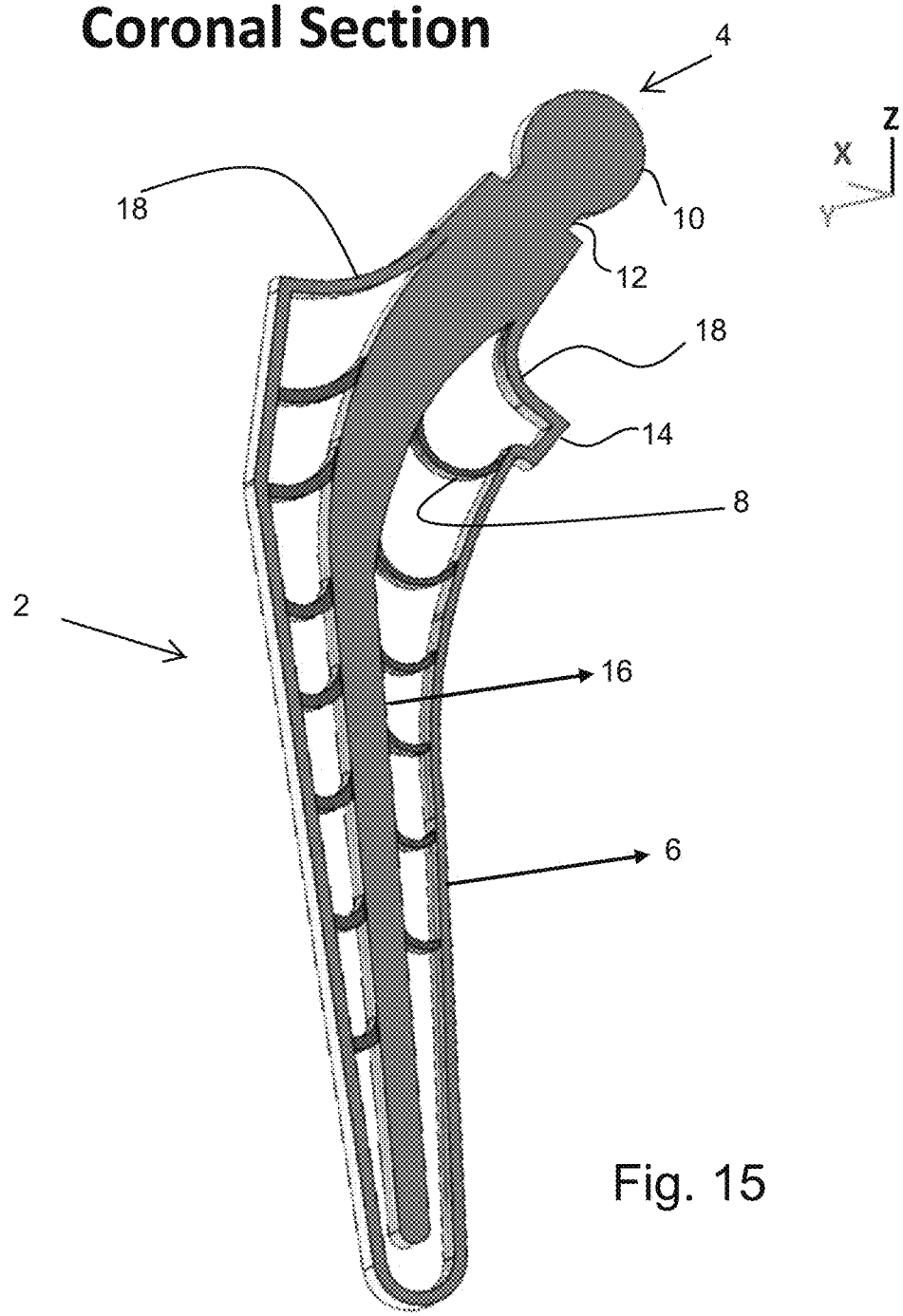
FIG. 15 is a cross section view of the load dissipating arthroplasty prosthesis of FIG. 14.
Figure 16:
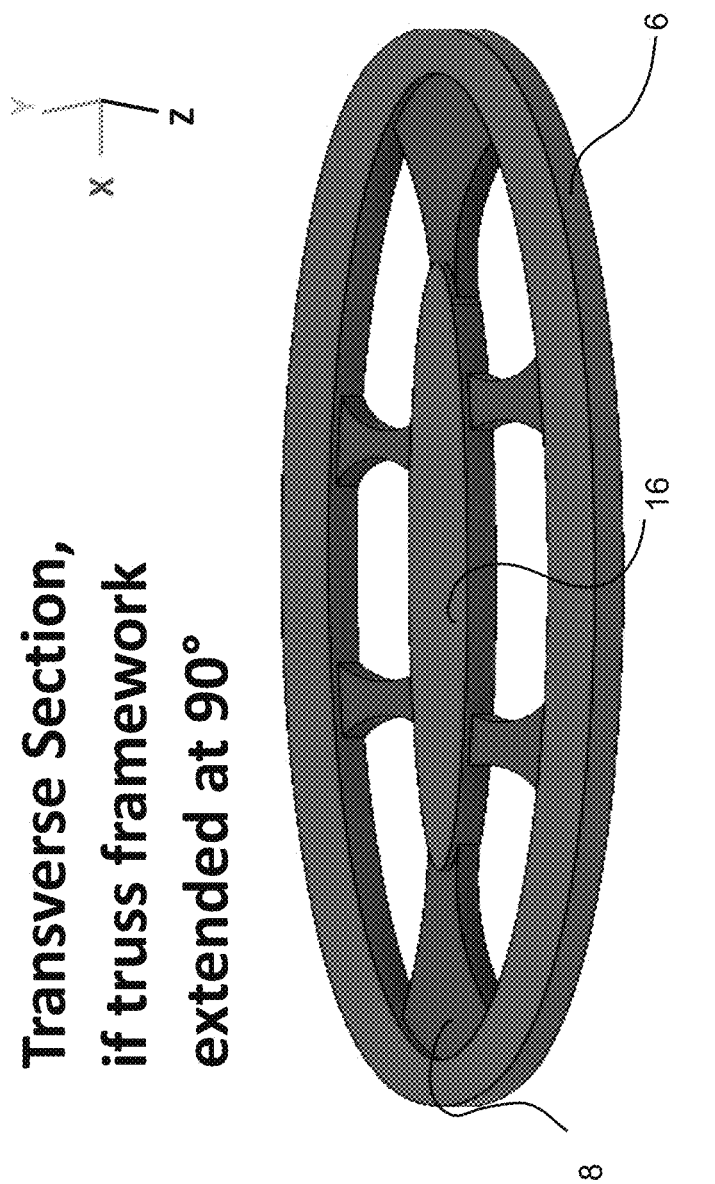
FIG. 16 is an isometric view of a transverse cross section of the load dissipating arthroplasty prosthesis of FIG. 14, but with the arcuate linkers/truss framework extended at 90 degrees from the shaft.
Figures 19A, 19B:
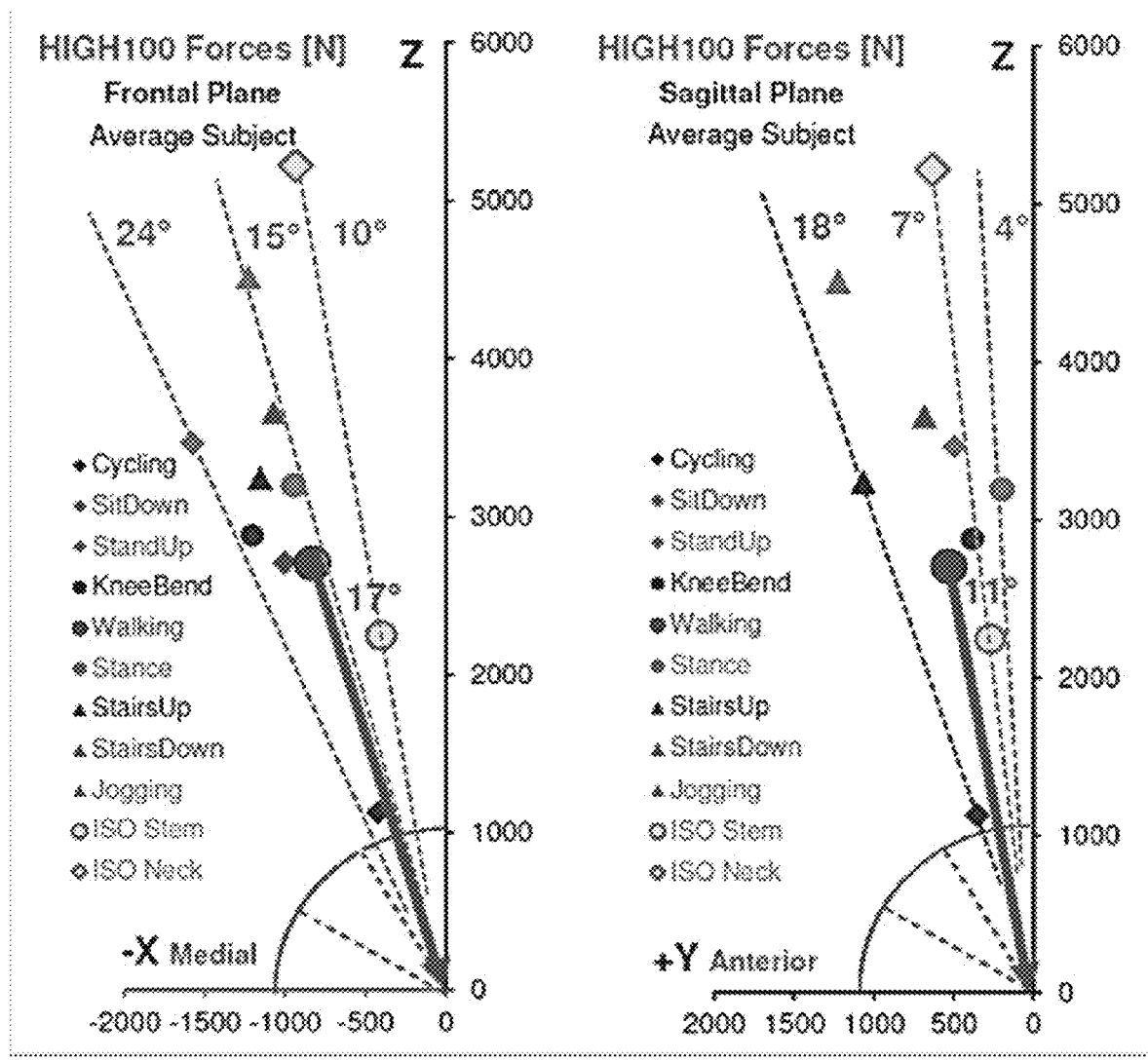
FIGS. 19A and 19B are load forces on frontal and sagittal planes respectively for human hip joints with various activities.

Additionally, unlike solid-form implants, implants based on the disclosed suspension designs will preferably have a removable cap (FIG. 2) to support implant insertion in the bone. The cap is a three sided structure, open of the fourth side, which straddles the perimeter of the shell. The cap engages with the perimeter of the shell via preferably 4 to 8, and most preferably 6 pins that interlock with corresponding non-through holes, or indents in the shell. The uppermost part of the cap (as depicted in FIG. 2) is preferably thicker or otherwise more robust to serve as an impact point for hammering the prosthesis into a space carved into the femur.

The circumference of the cap will engage an outer portion of the shell (preferably not the top-most trusses). The other possibility of a ring type cap around the neck to make the neck and shaft rigid during placement would work as well. In some embodiments the cap can be screw-on, a groove fit, or as shown pins on the cap engage indents on the shell. The cap is preferably removable, to be removed after implant is tapped into place.

The condylar head can be a screw-on or can be manufactured as one piece with the entire implant. The cap will encompass the condylar head and neck and engage with the shell for one-piece implants. In case of screw-on condylar head, the cap could encompass the neck and engage with the shell. Once the cap is removed, the condylar head may be screwed in place. The cap is primarily to facilitate implant placement.

As shown in FIGS. 20A and 20B, a further alternative embodiment of a load dissipating arthroplasty prosthesis is shown, in addition to or alternative to the arcuate linker-based model. The hatchwork on FIGS. 20A and 20B could be used to represent either alternative.

In one alternative the arcuate linker are replaced by an intermeshing network of metal webbing, the pattern of which resembles that seen in the native trabecular bone of the head of the femur. The network would span the distance between the shell and the shaft. The meshwork could be made from the same metal that the main unit is printed from or could be made from a second material that could be printed at the same time. The second material could be a currently used metal alloy that is currently approved for use in implants or of a novel, yet uncharacterized material that has yet to be utilized in this application.

Functionality of this embodiment of load dissipating arthroplasty prosthesis would be based on the specific pattern of the meshwork, the thickness of the mesh, the number of branches within the meshwork, the orientation of the mesh. This mesh would function in a bio similar fashion to the trabecular bone via load displacement along the length of the implant. The design of the meshwork would evolve from Finite Element Analysis studies derived from MRI information and information from high resolution cross-sectional analysis studies of cadaveric bone.

In a second further alternative, the distance between the outer shell and the inner shaft would be filled with a semi-rigid, highly crosslinked polymeric material which would be capable of absorbing and distributing loading forces along the length of the shell. This polymeric material could be uniform in composition or a layer structure using multiple polymeric materials possessing differential resistance to compressive loading and unloading.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A load dissipating arthroplasty prosthesis comprising:
   a shell;
   an articular device extending into the shell; and
   a shock absorber spacing and allowing limited movement between the shell and the articular device;
   wherein the shock absorber includes a plurality of arcuate linkers formed of leaf springs; and
   one of an inert gas and a vacuum fill an interior of the shell between the adjacent arcuate linkers.

2. The load dissipating arthroplasty prosthesis of claim 1, further comprising a collar covering an upper portion of the shell.

3. The load dissipating arthroplasty prosthesis of claim 2, wherein a first end of at least one of the plurality of arcuate linkers is attached to a shaft of the articular device, and a second end of the at least one of the plurality of arcuate linkers is attached to one of an inner surface of the shell and an inner surface of the collar.

4. The load dissipating arthroplasty prosthesis of claim 3, wherein the plurality of arcuate linkers attach to the shaft at a plurality of circumferential locations along the shaft and a plurality of axial locations along the shaft.

5. The load dissipating arthroplasty prosthesis of claim 4, wherein a lowest portion of the shaft is proximate to but spaced from a closest inner surface of the shell, such that under normal load, the lowest portion of the shaft does not impact the inner surface of the shell.

6. The load dissipating arthroplasty prosthesis of claim 4, wherein the shaft resiliently moves between 0.1 mm and 3.0 mm with respect to the shell when a force of between 700 to 5000 Newtons is applied to the shaft.

7. The load dissipating arthroplasty prosthesis of claim 4, wherein the collar is made of one of titanium metal and a titanium alloy.

8. The load dissipating arthroplasty prosthesis of claim 3, wherein the articular device passes through a collar aperture, the collar aperture being defined in the collar.

9. The load dissipating arthroplasty prosthesis of claim 8, wherein the collar aperture is located in a radially central location on the collar.

10. The load dissipating arthroplasty prosthesis of claim 8, wherein the shell has notches arranged along a circumference of the shell to engage with pins of a cap, the cap providing a point of impact to secure the prosthesis into a femur of a mammal.

11. The load dissipating arthroplasty prosthesis of claim 8, wherein the collar forms an upper membrane on the shell.

12. The load dissipating arthroplasty prosthesis of claim 8, further comprising a Z axis defined by the shaft, wherein the shaft is rotationally fixed about the Z axis with respect to the shell, allowing the shaft to resiliently increase obliquity about the collar aperture.

13. The load dissipating arthroplasty prosthesis of claim 3, wherein the arcuate linkers attach to the shell with a pedicel portion and arcuate linkers attach to the shaft with pedicel portions, each of the pedicel portions being one of wider, thicker, and both wider and thicker than a middle portion of the arcuate linkers.

14. The load dissipating arthroplasty prosthesis of claim 3, further comprising a plurality of medial arcuate linkers attaching a medial facing portion of the shaft to a medial portion of the shell, and a plurality of lateral arcuate linkers attaching a lateral facing portion of the shaft to a lateral portion of the shell.

15. The load dissipating arthroplasty prosthesis of claim 14, wherein the plurality of lateral arcuate linkers are one of greater in number, greater in size, and constructed out of a less flexible material than the plurality of medial arcuate linkers, or some combination thereof.

16. The load dissipating arthroplasty prosthesis of claim 1, wherein the shell has an outer surface that includes one of a porous metal and trabecular constructions.

17. The load dissipating arthroplasty prosthesis of claim 16, wherein the porous metal is one of titanium, tantalum, and an alloy including one of titanium, tantalum, and both titanium and tantalum, and a first end of the plurality of arcuate linkers attaches to the shaft at between 4 degrees and 30 degrees, as measured from an attachment location on the shaft, and
   a second end of the plurality of arcuate linkers attaches to the shell at between 4 degrees and 30 degrees, as measured from an attachment location on the shell.

18. The load dissipating arthroplasty prosthesis of claim 17, wherein the porous metal is one of
   a foam and
   coated with one of calcium phosphate, hydroxyapatite, derivatives of calcium phosphate, derivatives of hydroxyapatite, and combinations including one or more thereof.

19. A load dissipating arthroplasty prosthesis comprising:
   a shell;
   an articular device extending into the shell through a collar defined in the sell;
   a head and neck portion of the articular device extending from the collar;
   a shaft portion of the articular device extending into the shell;
   a plurality of shock absorbing arcuate linkers formed of leaf springs spacing and allowing limited movement between the shell and the articular device; the plurality of arcuate linkers having a first end, a second end, and an arcuate linker connecting the first and the second end;
   the first end of the plurality of arcuate linkers attaches to the shaft at less than 45 degrees, as measured from an attachment location on the shaft; and
   the second end of the plurality of arcuate linkers attaches to the shell at less than 45 degrees, as measured from an attachment location on the shell adjacent arcuate linkers are spaced from one another, wherein one of an inert gas and a vacuum fill an interior of the shell between adjacent arcuate linkers.

* * * * *